Figure 2:
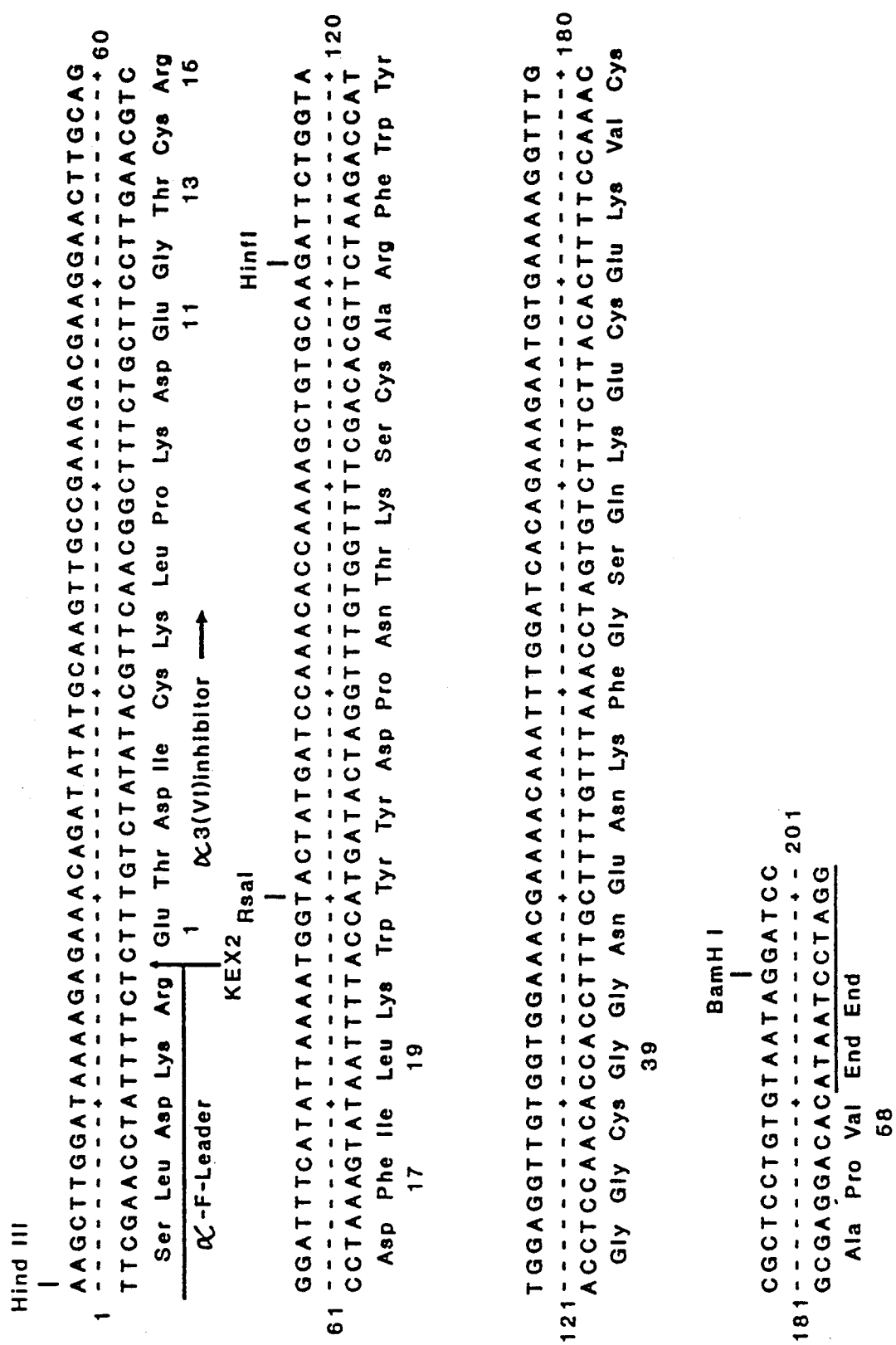

United States Patent [19]

Ebbers et al.

[11] Patent Number: 5,278,285
[45] Date of Patent: Jan. 11, 1994

[54] VARIANT OF KUNITZ-TYPE INHIBITOR DERIVED FROM THE α3-CHAIN OF HUMAN TYPE VI COLLAGEN PRODUCED BY RECOMBINANT DNA TECHNOLOGY

[75] Inventors: Juergen Ebbers; Dietrich Hoerlein, both of Wuppertal; Ruppert Timpl, Martinsried, all of Fed. Rep. of Germany; Mon-Li Chu, Philadelphia, Pa.

[73] Assignee: Bayer Aktiengesellschaft, Leverkusen, Fed. Rep. of Germany

[21] Appl. No.: 473,295

[22] Filed: Feb. 1, 1990

[51] Int. Cl.$^5$ ............................................. A61K 37/02
[52] U.S. Cl. ................................... 530/324; 435/69.2; 930/250
[58] Field of Search ........................ 930/250; 530/324; 435/69.2; 514/12

[56] References Cited

U.S. PATENT DOCUMENTS 4,371,466 2/1983 McGregor .................. 260/112.5 R

OTHER PUBLICATIONS

European J. of Biochemistry "Characterization of three constituent chains of collagen type VI . . ." Chu et al, vol. 168 pp. 309–317, 1987.
J. Biological Chem. "The Carboxyl Terminus of the Chicken α3 Chain of Collagen . . ." Bonaldo et al. vol. 264 (34) pp. 20235–20239, Dec. 5, 1989.
Methods in Enzymology, vol. XXXIV, "Affinity Techniques, Enzyme Purification: Part B", Bovine Trypsin and Thrombin, Hixson, Jr. and A. H. Nishikawa, pp. 440–448, Academic Press, 1974.
Methods in Enzymology, vol. XXXIV, "Affinity Techniques, Enzyme Purification; Part B", Chymotrypsin(s), Tomlinson, et al. pp. 415–420, Academic Press 1974.
Affinity Chromatography, Biospecific Sorption; Affinity Chromatography of Chymotrypsin on Soybean Trypsin Inhibitor Sepharose: Applications in genetics and Nuclide Labelling, Gabel, Kasche, Amneus and Lundqvist, pp. 99–102, Pergamon Press, 1977.
Applied Microbiology and Biotechnology, Springer-Verlag 1979, Biotechnol. 6; p. 195 (1979); "Recovery of Free Enzymes from Product Liquors by Bio-Affinity Adsorption: Trypsin Binding by Immobilised Soybean Inhibitor", Halling and Dunnill.
The Journal of Biological Chemistry, vol. 255, No. 15, Aug. 10, 1980 p. 7089, "Human Red Cell Purine Nucleoside Phosphorylase, Purification By Biospecific Affinity Chromatography and Physical Properties", Osborne, Mar. 17, 1980.
Hoppe-Seyler's Z. Physiol. Chem., vol. 361, p. 543, Apr. 1980, "Purification of Human and Bovine Alkaline Phosphatases by Affinity Chromatography", Mossner, Boll and Pfleiderer.
Analytical Biochemistry, vol. 107, p. 341, (1980), "Affinity Chromatographic Sorting of Carboxypeptidase A and its Chemically Modified Derivatives", Cveni Bazzone, Riordan & Vallee Mar. 31, 1980.
Hoppe-Seyler's Z. Physiol. Chem., vol. 359, p. 1019, Aug. 1978, "Affinity Chromatography of Bovine Bran β-Hexosaminidases with Substrate as Affinity Ligand," Lisman and Overdijk, May 1978.
Biochem. J. (1978), vol. 175, p. 125, "Purification of the Hexokinases by Affinity Chromatography on Sepharose-N-Aminoacylglucosamine Derivatives", Wright, Warsy, Holroyde and Trayer, Feb. 1978.
Archives of Biochemistry and Biophysics, vol. 198, No. 2, Dec., 1979, p. 533, "Quantitative Affinity Chromatography of α-Chymotrypsin", Dunn and Gilbert, Aug. 10, 1979.
Understanding Enzymes, Third Ed. (Horwood Press, 1991), pp. 309–310, Trevor Palmer.

Primary Examiner—Robert J. Hill, Jr.
Assistant Examiner—Laurie Scheiner
Attorney, Agent, or Firm—Sprung Horn Kramer & Woods

[57] ABSTRACT

Kunitz-type inhibitor derived from the α3-chain of human type VI collagen produced by recombinant DNA technology, variants thereof, process, expression vector and recombinant host therefore and pharmaceutical use thereof are disclosed.

1 Claim, 4 Drawing Sheets

```
      GAAACAGATATATGCAAGTTGCCGAAAGACGAAGGAACTTGCAG GGATTCATATTAAAA
  1*--+---------+---------+---------+---------+---------+--------+ 60
      CTTTGTCTATATACGTTCAACGGCTTTCTGCTTCCTTGAACGTCCCTAAAGTATAATTTT
      Glu Thr Asp Ile Cys Lys Leu Pro Lys Asp Gly Thr Cys Arg Asp Phe Ile Leu Lys
       1                   11          13          15          17          19

RsaI                              HinfI
               |                                  |
      TGGTACTATGATCCAAACACCAAAAAGCTGTGCAAGATTCTGGTATGGAGGTTGTGGTGGA
 61---+---------+---------+---------+---------+---------+--------+ 120
      ACCATGATACTAGGTTTGTGGTTTTCGACACGTTCTAAGACCATACCTCCAACACCACCT
      Trp Tyr Tyr Asp Pro Asn Thr Lys Ser Cys Ala Arg Phe Trp Tyr Gly Gly Cys Gly Gly
                                                                                  39

AACGAAAAACAAATTTGGATCACAGAAAGAATGTGAAAAGGTTTGCGCTCCTCCTGTGCTCCGCC
121---+---------+---------+---------+---------+---------+--------+ 180
      TTGCTTTTGTTTAAACCTAGTGTCTTTCTTACACTTTTCCAAACGCGAGGACACGAGCGG
      Asn Glu Asn Lys Phe Gly Ser Gln Lys Val Cys Glu Lys Val Cys Ala Pro Val Leu Ala
                                                                              58

AAACCCGGAGTCATCAGTGTGATGGGAACC
181---+---------+---------+------+ 210**
      TTTGGGCCTCAGTAGTCACACTACCCTTGG
      Lys Pro Gly Val Ile Ser Val Met Gly Thr
                                          70
```

\* = aminoacid pos. 2873
\*\* = aminoacid pos. 2943

FIG. 1

VARIANT OF KUNITZ-TYPE INHIBITOR DERIVED FROM THE α3-CHAIN OF HUMAN TYPE VI COLLAGEN PRODUCED BY RECOMBINANT DNA TECHNOLOGY

The present invention describes a novel Kunitz type proteinase inhibitor (α3(VI)-inhibitor) derived from a cDNA of the type VI collagen α3 chain and peptide variants thereof. In addition a process for preparing the inhibitor and variants thereof by rec. DNA technology as well as pharmaceuticals containing these peptides are described. The α3(VI) inhibitor variants are characterized by their ability to inhibit serine proteases such as plasma kallikrein and pancreatic and leucocyte elastase.

Well balance levels and tightly controlled interactions of human proteinases and proteinase inhibitors are an important prerequisite for the common healthy state of the human organism.

If, for example, lysosomal proteases reach the extracellular space they are normally rapidly trapped by potent endogenous inhibitors such as α1 proteinase inhibitor (Travis and Salvesen, Ann. Rev. Biochem. 52, 655 (1983)).

In certain pathological conditions the adequate levels of extracellular proteinase and proteinase inhibitors may be disturbed by excessive release of lysosomal proteinases, such as leucocyte elastase.

The consequence may be an extensive proteolytic degradation of connective tissues as well as of humoral proteins including coagulation-, fibrinolysis-, and complements-factors by elastase and other lysosomal proteinases leading to severe clinical symptoms like emphysema, shock lung, ARDS and coagulation disorders.

Another example for the pathological consequences of proteinase inhibitor deficiency has been described in studies relating to haemostatic defects associated with cardiopulmonary bypass operations.

Recent investigations have shown that during continuous extracellular circulation of the blood extensive contact activation of plasma kallikrein occurs, which is normally inhibited by the endogenous C1-esterase inhibitor. In case of C1-esterase reduction plasma kallikrein seems to induce the coagulation cascade, the fibrinolytic system and the platelet receptor break down (Colman, J. Clin. Invest. 73, 1249-1253, (1984); Heller et al., Thromb. Haemostas. 62, 269 (1989); Hauert et al., Blood 73, 944-999 (1989); Wachtfogel et al., Blood 73, 468-471 (1989)).

In order to reduce the risk of internal bleeding following heart surgery the patients must therefore be supplied with high amounts of foreign blood.

Recently performed clinical studies have shown that the application of the bovine proteinase inhibitor aprotinin (Trasylol ®) during open heart surgery reduces blood loss significantly (Bistrup et al., Lancet I, 366-367 (1988); Royston et al., paper submitted to: J. Cardiothorac. Anaesth. (1989)).

Regarding the examples described above, various synthetic and naturally occuring proteinase inhibitors are being studied as potential therapeutics for uncontrolled proteinase activities.

In experimental models of sepsis and emphysema synthetic elastase inhibitors (Powers, Ann. Rev. Respir. Dis. 127, 554-558 (1983)) and natural inhibitors of animal origin such as eglin C (Schnebli et al., Europ. J. Respir. Dis. 66, Suppl. 139, 66-70 (1985) or Hirudin have been shown to be therapeutically useful.

However, in order to avoid toxic side effects and especially allergic reactions when a prolonged therapy is necessary the application of a proteinase inhibitor of human origin is preferable.

The present invention describes a new Kunitz type proteinase inhibitor of human origin, whose aminoacid sequence was deduced from 3 cDNA clones which cover 3 kb of the type VI collagen α3 chain mRNA. The cDNA was isolated from a placenta and a fibroblast cDNA library.

The selected proteinase inhibitor domain is located in the last 70 aminoacid residue segment of the globular C5 domain of the type VI collagen α3 chain (aminoacid pos. 2873-2943, FIG. 1).

Surprisingly it was found that this segment shows 40-50% sequence homology to many Kunitz-type inhibitors such as the bovine trypsin inhibitor aprotinin (Kassell and Laskowski, Biochem. Biophys. Res. Com. 20, 463-468 (1965); Laskowski and Kato, Ann. Rev. Biochem. 49, 593-626 (1980)), the human urinary trypsin inhibitor (Wachter and Hochstrasser, Hoppe-Seyler's Z. Physiol. Chem. 362, 1351-1355 (1981)), the lipoprotein-associated coagulation inhibitor (Wun et al., J. Biol. Chem. 263, 6001-6004 (1988)) and the recently described amyloid protein (Ponte et al., Nature 331, 525-527 (1988); Tanzi et al., Nature 331, 528-530 (1988)).

Furthermore it was found that the cDNA sequence covering the aminoacid pos. 2873 to 2931 of the C5 domain of the type VI collagen α3 chain, when cloned for example in an appropriate, self replicating yeast vector under the control of regulatory sequences for gene expression, is expressed in transformed yeast. The resulting product, called α3(VI) inhibitor, is biologically active and inhibits human trypsin.

Using state-of-the-art rec. DNA technology it was furthermore found that by replacement of one or more of certain aminoacids in and/or around the active center of the α3(VI) inhibitor specific and potent inhibitors of human plasma kallikrein, pancreatic and leucocyte elastase could be obtained. Therefore, the present invention also relates to synthetic peptide variants of the α3(VI) inhibitor produced by rec. DNA technology.

Furthermore the present invention relates to α3(VI) inhibitor variants in which, besides replacements in one or more positions in and/or around the active center, additional extensions and/or deletions are introduced. Additional modifications of this type may further improve the desired inhibitory properties, result in more favorable pharmacokinetic behaviour, prolong the in vivo half-life or result in a better producibility.

Preferred is a Kunitz-type proteinases inhibitor in which the aminoacid residue in one or more of pos. 11, 12, 13, 14, 15, 16, 17, 18, 19 and pos. 39 is replaced by other naturally occuring aminoacids.

Useful aminoacids for that purpose are selected from the group Ala, Gly, Ile, Leu, Phe, Val, Arg, Tyr, Trp and Lys.

Particularly preferred is the Kunitz-type proteinase inhibitor from the group
  Ala16-Arg17-Arg39-inhibitor
  Ala16-Ala17-Arg39-inhibitor
  Ala16-Arg17-Gly39-inhibitor
  Ala16-Ala17-Gly39-inhibitor The present invention is also related to fragments with proteinase inhibitory activity, which are obtained from the Kunitz-type proteinase inhibitors.

The invention is further related to pharmaceutical compositions containing the Kunitz-type proteinase inhibitors.

Another embodiement of the present invention is a process for producing any of the proteinase inhibitors characterized by i) transformation of procaryotes or lower eucaryotes with suitable expression vectors comprising a DNA sequence, which encodes the proteinase inhibitor, ii) cultivating the transformants and iii) recovering the produced proteinase inhibitor from the fermentation.

In a preferred process S. cerevisiae is the transformed and cultivated lower eucaryote.

The expression of peptide variants of α3(VI) inhibitor or of fragments of α3(VI) inhibitor can be carried out in bacterial or lower eucaryotic systems. Thus, suitable among bacterial systems are for example Escherichia coli K 12 strains. In these types of systems the peptide or its variants may be expressed intracellularly (unfused or fused to a suitable fusion partner such as the N-terminal part of the MS2 replicase) or else may be secreted into the periplasmic space by using suitable signal peptides (for example the OmpA signal sequence).

Suitable among the eucaryotic systems are, for example, yeast systems in which the expression product is either accumulated intracellularly or secreted into the extracellular space (for example with the alpha mating factor pre-pro-sequence).

However, it is additionally possible to use many other pro- and eucaryotic expression systems, for example strains of Bacillus, Staphylococcus, Hansenula, Aspergillus or other host strains.

The present invention also includes pharmaceutical compositions and preparations comprising the peptides as outlined above and said pharmaceutical compositions are very useful as part of the therapeutic regimen e.g. in pathophysiological conditions as described above.

Methods
Enzymes

The enzymes used for rec. DNA-technology were obtained from Boehringer Mannheim, Biolabs and Pharmacia.

Standard Methods

The standard methods used for cleavage of DNA with restriction enzymes, for gelelectrophoresis of DNA, for isolation and ligation of DNA fragments, for the transformation of E. coli bacteria and for the isolation of plasmid and bacteriophage DNA from E. coli are described by Sambrook et al., Molecular Cloning, 2nd edition, Cold Spring Habor (1988).

Chemical synthesis of DNA-oligonucleotides

The DNA-oligonucleotides for gene constructions and site directed mutagenesis were synthesized in an Applied Biosystems DNA-synthesizer (model 380A) using established phosphoramidite chemistry. The oligonucleotides were purified by denaturating polyacrylamid gel electrophoresis.

DNA sequencing

To verify the DNA sequence of individual gene constructions, single stranded DNA subcloned in M13-bacteriophage vectors was sequenced by the method of Sanger et al., Procl. Nat. Acad. Sci. 74, 5463-5467 (1977).

Site directed mutagenesis

Site directed mutagenesis of specific DNA codons or gene fragments was performed according to the method of Taylor et al., Nucl. Acids Res. 13, 8764-8785 (1985) by using the commercially available mutagenesis kit from Amersham-Buchler (code no. RPN. 2322).

Yeast transformation

Transformation of lithium-treated yeast cells was carried out in accordance to the method described by Sherman et al., Methods in Yeast Genetics, Cold-Spring-Harbor (1986). Yeast transformants were generally obtained on selective media after an incubation period of 3 days at 30° C.

Growth of transformants and analysis of secretion products

Transformants were cultivated in SD medium (0.67% yeast nitrogen base without aminoacids, 2% D-glucose) supplemented with threonine, methionine and histidine (20 mg/liter each) at 30° C. After an adequate cell density had been reached, the cells were spun down, and the trypsin-inhibiting activity in the culture supernatant was measured.

Polyacrlyamide gel electrophoresis

Proteins were normally detected by SDS polyacrylamide gel electrophoresis (Laemmli, Nature 277, 680, 1970) and staining with Coomassie brilliant blue.

Aminoacid analysis

About 1 nmol of protein was incubated in the presence of 200 µl of 6M HCl, 0.05% β-mercaptoethanol at 110° C. under vacuum for 22 h. The hydroysates were dried, dissolved in 150 µl of 0.2M sodium citrate buffer, ph 2.2, and filtered. Aminoacid analysis was carried out in a Biostronic LC 5000 aminoacid analyser with fluorescence detector and Shimadzu C-R2AX integrator. The aminoacids were quantified after reaction with phthaladehyde in accordance with the literature (Benson & Hare, Proc. Natl. Acad. Sci., USA 72, 619 (1975)).

Aminoacid sequencing 1-2 nmol of protein dissolved in 30 µl of trifluoroacetic acid were applied to Polybrene-treated glass fibre filters and sequenced in a gas-phase sequenator (Applied Biosystems) by the method of Hewick et al., J. Biol. Chem. 256, 7990 (1981). Phenylthiohydantoin derivatives were separated an analyzed with the aid of a cyano HPLC column (DuPont) as described by Beyreuther et al., Modern Methods in Protein Chemistry, 303-325, Walter de Gruyter, Berlin (1983), using a Waters HPLC system.

Trypsin inhibition assay

The trypsin activity was determined using the method of geiger & Fritz, Methods of Enzymatic Analysis, Vol. V, 3rd ed., Bergmeyer (ed.), Verlag Chemie, Weinheim (1984), p. 121 with benzoyl-L-arginine p-nitroanilide as substrate. The liberated p-nitroaniline was measured in a spectrophotometer at 405 nm. Enzyme and inhibitor were preincubated for 15 min before addition of the substrate.

Elastase inhibition assay

Human leucocyte elastase was obtained from Elastin Products Company Inc., P.O. Box 147, Pacific, Miss., 63069/USA. The substrate used was MeOSuc-Ala-Ala-Pro-Val-pNA (Bachem, Budendorf, Switzerland). The assay conditions are indicated in Table 3. In general, the inhibitor samples were diluted with assay buffer, enzyme was added and the mixture was then preincubated. The reaction was started by addition of substrate (dissolved in DSMO in a concentration of 0,1M and adjusted to the concentration of the stock solution with buffer), and the liberation of p-nitroaniline from the substrate was continuously followed at 405 nm. 100% values were determined in corresponding assays without inhibitors. The inhibition (in percent) was calculated from the following equation.

$$\% \text{ Inhibition} = 100 \times \left(1 - \frac{\text{OD in the presence of inhibitor}}{\text{OD in the absence of inhibitor}}\right)$$

Assay conditions (Nakajima et al., J. Biol. Chem. 254, 4027 (1979):

| Buffer | 0.2M Tris/HCl, pH 8.0 + 0.1% Tween 80 |
|---|---|
| Total volume after addition of substrate | 0.65 ml |
| Enzyme quantity/assay | 50 ng |
| Preincubation time at room temperature | 30 min |
| Substrate Stock solution Quantity/assay | MeO—Suc—Ala—Ala—Pro—Val—pNA 0.065M 0.1 ml |
| Assay temperature | 30° C. |

Plasma kallikrein inhibition assay

Plasma kallikrein (0.12 U/ml in Tris buffer) was preincubated with the rec. proteinase inhibitor for 5 minutes. Afterwards the substrate H-D-Pro-Phe-Arg-pNA (S-2302, 4 mM/L) was added to a final volume of 1 ml. After an incubation time of 5 minutes the amount of released p-NA was measured photometrically at 405 nm.

Plasma kallikrein and the substrate S-2302 were obtained from AB Kabi Diagnostica (Sweden). The assay was performed in 45 mM/L Tris buffer, 0.05% Tween 80, pH 8.0 at 30° C.

EXAMPLE 1

Construction of the α3(VI) inhibitor master gene

A synthetic DNA-sequence of the natural α3(VI) inhibitor master gene was derived from a human type VI collagen cDNA clone encoding a 58 residue part of the C-terminal globular domain C5 (aminoacid pos. 2873-2931, FIG. 1).

For in frame fusion with the yeast α-mating factor leader sequence the 5'-end of the α3(VI) inhibitor master gene was extented with a 16 bp DNA adapter containing the 3'-end of the α-mating factor leader sequence and a HindIII restriction site. The 3'-end of the gene was extended with a 11 bp DNA sequence containing two translation stop codons and a BamHI restriction site (see FIG. 2).

The α3(VI) inhibitor master gene was constructed from the 6 oligonucleotides described below:

540 -phosphorylated oligonucleotides 1 to 6 by heating for 5 minutes at 90° C. followed by cooling to 20° C. over a period of 60 minutes.

The duplexes A, B and C were mixed in equal amounts and treated with T4-ligase overnight. The α3(VI) inhibitor master gene was isolated as a 201 bp DNA fragment after electrophoresis of the ligation mixture on a 2% agarose gel.

Figure 3:
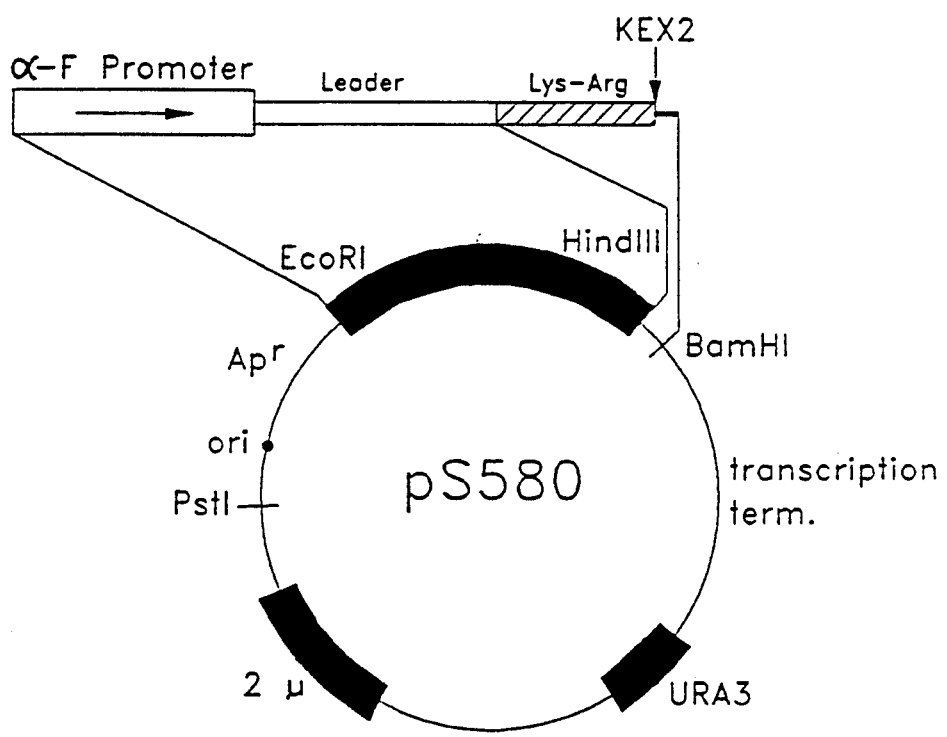

Thereafter the synthetic inhibitor master gene with the 5'- and 3'-DNA extensions (FIG. 2) was integrated downstream of the α-mating factor leader sequence into the HindIII and BamHI restriction sites of the E. Coli-1 -yeast-shuttle vector pS580 (FIG. 3 and 4).

The DNA sequence of the S. cerevisiae α-mating-factor leader sequence up to the KEX2 processing site and the construction of the shuttle vector pS580 is described in the German patent application no. P 39 305 22.8.

For DNA sequencing and site directed mutagenesis the 3(VI) inhibitor gene was subcloned into the HindIII-BamHI restriction sites of the bacteriophage vector M13 mp18. The sequence of the inhibitor master gene was confirmed by DNA-sequencing (FIG. 2).

Figure 4:
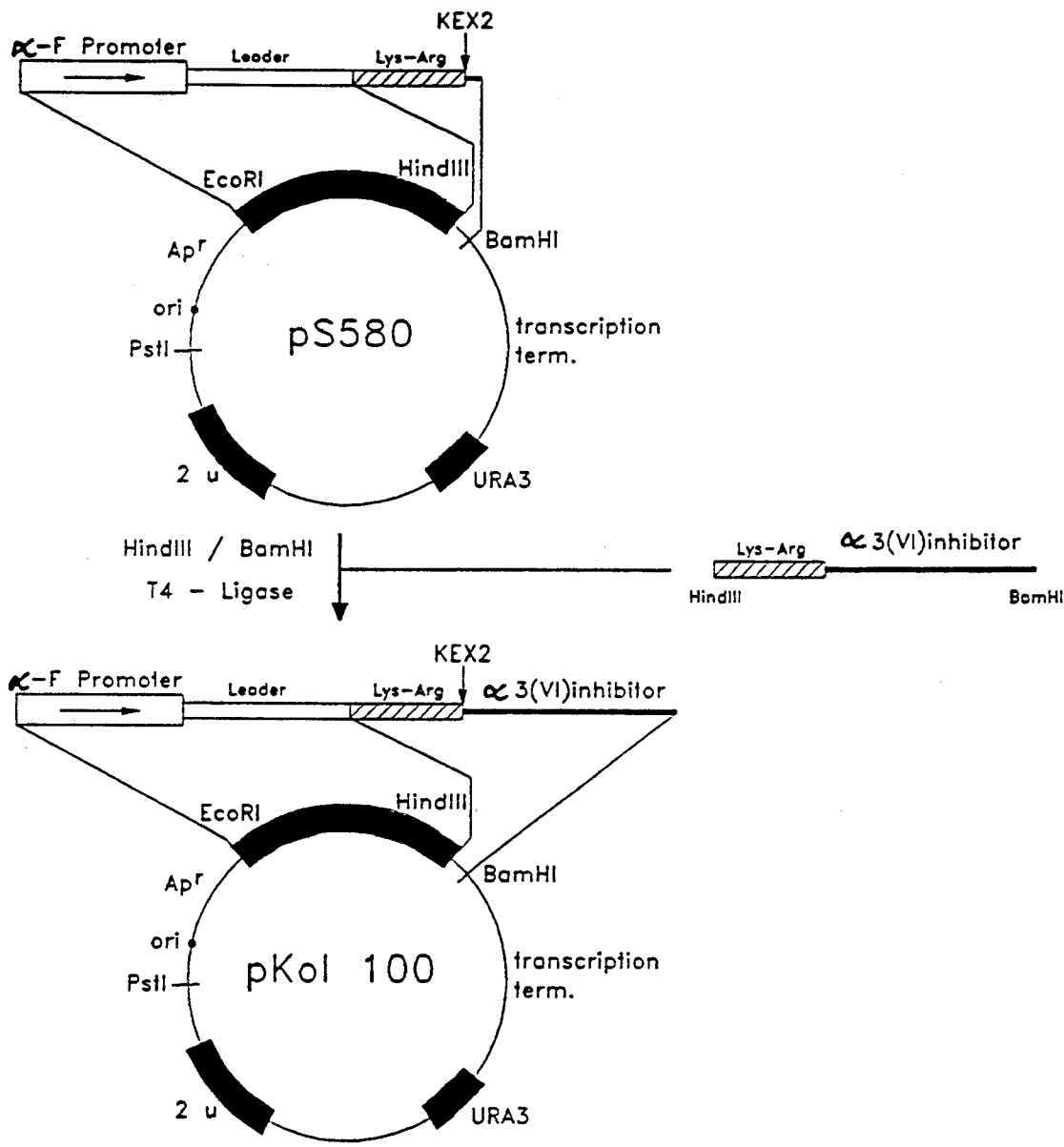

Competent E. coli K12-bacteria was transformed with the plasmid vector pKol 100 inhibitor containing the inhibitor gene (see FIG. 4). Selection was done on ampicillin resistance.

Purified plasmid DNA of pKol 100 was used for the transformation of the S. cerevisiae strain SC106 (Mat, hom3, gal2, his6, ura3) strain S2207A, Yeast Genetics Stock Center, University of California, Berkeley/USA). Single yeast colonies were selected on URA⁻-SD-agar plates for fermentation purposes.

EXAMPLE 2

Construction of α3(VI) inhibitor variants

For exchanging aminoacids in the active center of the α3(VI) inhibitor site directed mutagenesis was carried out on the inhibitor master gene which was cloned in the bacteriophage vector M13 mp18.

After transfection of E. coli strain TG1 (K12, (lacpro), supE, thi, hsdD5/F'traD36, proA+B+, lacZ M15) single stranded template DNA of the rec. bacteriophage vector M13 mp18 containing the inhibitor master gene was harvested.

According to the method described above a commercially available mutagenesis kit from Amersham Buchler, code no. RPN 2322, was used for codon exchange.

For the mutagenesis experiments the following synthetic DNA-primers were used for the construction of the α3(VI) inhibitor variants:

```
1  5'-AGC TTG GAT AAA AGA GAA ACA GAT ATA TGC AAG TTG
      CCG AAA GAC GAA GGA ACT TGC AGG GAT TTC ATA-3'

2  5'-T TAA TAT GAA ATC CCT GCA AGT TCC TTC GTC TTT
      CGG CAA CTT GCA TAT ATC TGT TTC TCT TTT ATC CA-3'

3  5'-TTA AAA TGG TAC TAT GAT CCA AAC ACC AAA AGC TGT
      GCA AGA TTC TGG TAT GGA GGT T-3'

4  5'-CC ACA ACC TCC ATA CCA GAA TCT TGC ACA GCT TTT
      GGT GTT TGG ATC ATA GTA CCA TT-3'

5  5'-GT GGT GGA AAC GAA AAC AAA TTT GGA TCA CAG AAA
      GAA TGT GAA AAG GTT TGC GCT CCT GTG TAA TAG-3'

6  5'-G ATC CTA TTA CAC AGG AGC GCA AAC CTT TTC ACA
      TTC TTT CTG TGA TCC AAA TTT GTT TTC GTT TCC A-3'
```

10 μg of each of the duplexes A (1+2), B (3+4), C (5+6) was obtained from the corresponding pairs of the Leu15-Ala16-Leu17-variant:

1  5'-GAC GAA GGA ACT TGC CTT GCT CTT ATA TTA AAA
                         Leu Ala Leu
   TGG TAC-3'

Val15-Ala16-Leu17-variant:

2  5'-GAC GAA GGA ACT TGC GTT GCT CTT ATA TTA AAA
                         Val Ala Leu
   TGG TAC-3'

Ala16-Ala17-Arg39-variant:

3  5'-GAA GGA ACT TGC AGG GCT GCT ATA TTA AAA TGG-3'
                         Ala Ala 4  5'-GGA GGT TGT AGA GGA AAC GAA
                Arg

Ala16-Arg17-Arg39-variant:

5  5'-GAA GGA ACT TGC AGG GCT AGA ATA TTA AAA TGG-3'
                         Ala Arg 6  5'-GGA GGT TGT AGA GGA AAC GAA
                Arg

The sequence of the α3(VI) inhibitor muteins was confirmed by DNA sequencing.

For expression in yeast the α3(VI) inhibitor muteins were separately cloned in the HindIII-BamHI restriction site of the *E. coli*-yeast-shuttle vector pS580.

Afterwards the *S. cerevisiae* strain JC106 was transformed with the new vector constructions pKol 101 (containing Leu15-Ala16-Leu17-α3(VI) mutein), pKol 102 (containing Val15-Ala16-Leu17-α3(VI) mutein), pKol 103 (containing Ala16-Arg17-Arg39-α3(VI) mutein) and pKol 104 (Ala16-Ala17-Arg39-α3(VI) mutein). Selection and separation of yeast transformants was done as described before.

EXAMPLE 3

Expression of the rec. α3(VI) Inhibitor Master Gene and rec. α3(VI) Inhibitor Muteins Selected colonies of the yeast strain SC106 transformed with plasmid-DNA of pKol 100, pKol 101, pKol 102, pKol 103 and pKol 104 were cultivated to shake flasks and 1 L-fermenters under including conditions. Probes of the culture supernatants were tested for trypsin inhibition activity, elastase inhibition activity and plasma kallikrein inhibition activity.

The results which were obtained showed that 1-5 mg/L of the α3(VI) inhibitor as well as the α3(VI) inhibitor variants were secreted from yeast.

EXAMPLE 4

Purification of the Ala16-Arg17-Arg39-variant of the α3(VI)-Kunitz inhibitor

The supernatant of the 1 L-fermentation of the Ala16-Arg17-Arg39-variant was adjusted with concentrated citric acid to pH 3,0 and then diluted with water to a conductivity of 6,0 mS/cm. The resulting solution was then applied to a column containing 50 ml of S-Sepharose ff equilibrated in 50 mM Na-citrated pH 3. The column was washed successively with 5 volumes of 50 mM Na-citrate and 5 volumes of 50 mM TRIS HCl pH 7,5. Finally the column was equilibrated with 20 mM Hepes pH 6,0 and the material eluted with 20 mM Hepes pH 6,0 containing 0,4M NaCl.

Eluted material was dialyzed overnight against 20 mM Hepes pH 6,0 until the conductivity was 1,0 mS/cm and applied to a column of 20 ml S-Sepharose HP equilibrated in 20 mM Hepes pH 6,0.

The column was developed with a gradient of 0 to 0,5M NaCl in 20 mM Hepes pH 6,0. Fractions containing the inhibitor were pooled and applied directly to an HPLC-column filled with Vydac-C18 (300 A)-resin and equilibrated with 0,1% TFA. The material was then eluted with a gradient of 0 to 60% Acetonitril in 0,1% TFA.

Fractions were collected, diluted 1:1 with water and lyophilized.

All through the purification the inhibitor was detected by either SDS-PAGE or trypsin inhibition assay.

Average yields of the purification were around 40% of the activity originally present in the cell culture supernatant.

From lyophilized material a number of analysis were performed to verify the identify of the inhibitor (e.g. gel-electrophoresis, amino acid composition, N-terminal sequencing).

The biological activity of the purified Ala16-Arg17-Arg39-α3(VI) inhibitor was shown in a plasma kallikrein and a trypsin inhibition assay.

FIGURE LEGENDS

FIG. 1: Nucleotide and deduced aminoacid sequence of the last 70 aminoacid residue segment of the C5-domain of the type VI collagen α3-chain (aminoacid pos. 2873-2943), which contains the Kunitz type inhibitor domain.

FIG. 2: Nucleotide and aminoacid sequence of the α3(VI)-Kunitz type inhibitor modified for gene expression with additional 5'0 and 3'-extensions. The DNA extensions containing the HindIII and BamHI restriction site and the sequence encoding the KEX2 processing site of the α-mating factor leader sequence. The DNA extensions are underlined. The KEX2-enzyme processing site is marked by an arrow.

FIG. 3: Restriction map of the *E. coli*-yeast shuttle vector pS580.

FIG. 4: Construction of the plasmid vector pKol 100 containing the α3(VI)-Kunitz type inhibitor master gene.

What is claimed is:

1. A modified Kunitz-type proteinase inhibitor consisting of the amino acid sequence shown in FIG. 1 modified at positions 16, 17 and 39 as follows:

Ala16-Arg17-Arg39.

* * * * *